(12) United States Patent
Krim et al.

(10) Patent No.: US 9,241,840 B2
(45) Date of Patent: Jan. 26, 2016

(54) TAMPON HAVING SATURATION INDICATOR

(71) Applicants: Jacqueline Sue Krim, Raleigh, NC (US); Louis Lindsey Crawley, Raleigh, NC (US)

(72) Inventors: Jacqueline Sue Krim, Raleigh, NC (US); Louis Lindsey Crawley, Raleigh, NC (US)

( * ) Notice: Subject to any disclaimer, the term of this patent is extended or adjusted under 35 U.S.C. 154(b) by 10 days.

(21) Appl. No.: 14/158,970

(22) Filed: Jan. 20, 2014

(65) Prior Publication Data

US 2014/0309605 A1 Oct. 16, 2014

Related U.S. Application Data

(60) Provisional application No. 61/811,829, filed on Apr. 15, 2013.

(51) Int. Cl.
*A61F 13/15* (2006.01)
*A61F 13/42* (2006.01)
*A61F 13/34* (2006.01)
*A61F 13/20* (2006.01)

(52) U.S. Cl.
CPC .............. *A61F 13/42* (2013.01); *A61F 13/20* (2013.01); *A61F 13/208* (2013.01); *A61F 13/34* (2013.01)

(58) Field of Classification Search
CPC . A61F 13/15211; A61F 13/20; A61F 13/208; A61F 13/34; A61F 13/42; A61F 13/84; A61F 13/8405; A61F 2013/15235; A61F 2013/8408; A61F 2013/8497
USPC .............................. 604/359, 360, 361, 385.18
See application file for complete search history.

(56) References Cited

U.S. PATENT DOCUMENTS 3,624,746 A 11/1971 Grad
3,794,024 A * 2/1974 Kokx et al. .................... 604/361
(Continued)

FOREIGN PATENT DOCUMENTS

WO 0072792 A1 12/2000

OTHER PUBLICATIONS

U.S. DHHS, FDA, Center for Devices & Radiological Health; Obstetrics & Gynecology Devices Branch, Division of Reproductive, Abdominal, and Radiological Devices, Office of Device Evaluation: "Guidance for Industry and FDA Staff, Menstrual Tampons and Pads: Information for Premarket Notification Submissions (510(k)s)"; Jul. 27, 2005, Division of Dockets Management, Food and Drug Administration, Rockville, Maryland. Entire Document.
(Continued)

*Primary Examiner* — Lynne Anderson
(74) *Attorney, Agent, or Firm* — Carla Gannon Law

(57) ABSTRACT

An improved absorbent hygiene article, such as a tampon, has a detachably connected saturation indicator. The saturation indicator is calibrated, and preferably indicates the degree of saturation of the corresponding article by staining or swelling. One may check saturation of the hygiene article through various means including visual or tactile inspection of the indicator after it has been pulled out of the article. In this manner it is possible, without having to remove the article, to determine whether or not it is advisable to change the article. In one embodiment, the saturation indicator is detachably connected to the underlying article by an adhesive that releases when it becomes moist. In this manner the inability to easily remove the indicator is, in itself, an indication of lack of saturation beyond a predetermined threshold.

16 Claims, 5 Drawing Sheets

(56) References Cited

U.S. PATENT DOCUMENTS

| | | | |
|---|---|---|---|
| 6,506,958 B2* | 1/2003 | Williams | 604/361 |
| 6,596,919 B2* | 7/2003 | Williams | 604/361 |
| 7,214,848 B2* | 5/2007 | DiSalvo et al. | 604/361 |
| 7,806,882 B1* | 10/2010 | Larkin | 604/385.18 |
| 8,247,638 B2* | 8/2012 | Kim et al. | 604/361 |
| 2004/0064116 A1* | 4/2004 | Arora et al. | 604/361 |
| 2004/0199132 A1* | 10/2004 | DiSalvo et al. | 604/361 |
| 2005/0055003 A1* | 3/2005 | Bittner et al. | 604/385.18 |
| 2006/0229577 A1* | 10/2006 | Roe | A61F 13/42 604/361 |
| 2008/0033383 A1* | 2/2008 | Cantor et al. | 604/361 |
| 2013/0231626 A1 | 9/2013 | Riordan | |

OTHER PUBLICATIONS

Blieszner, Kathleen, Ph.D., Regulatory Affairs Manager, The Procter & Gamble Company (Cincinatti, OH), Section 510(k) pre-market notification of intent to market TAMPAX® V Plastic Applicator Tampons, unscented; and Fisher, Benjamin R., Director, Division of Reproductive, Gastro-Renal, and Urological Devices, Office of Device Evaluation, Center for Devices and Radiological Health (Silver Spring, MD); Letter in response to approval request. Entire Document.

Absorbent Hygiene Products Manufacturers Association (AHPMA), UK Code of Practice for Tampon Manufacturers & Distributors, Version 4, Feb. 20, 2009, AHPMA, 46 Bridge Street, Godalming, Surrey, UK GU7 1HL. Entire Document.

www.coatsindustrial.com, Tampon Strings Product Line Info., Coats Industrial Thread Limited, 1 The Square, Stockley Park, Uxbridge, Middlesex, UB11 1TD, England. Entire Document.

Written Opinion of the International Searching Authority, mailed Aug. 4, 2014, regarding PCT/US2014/27027, Louis Lindsey Crawley.

* cited by examiner

TAMPON HAVING SATURATION INDICATOR

CROSS-REFERENCE TO RELATED APPLICATIONS

This application claims the benefit of U.S. Provisional Application 61/811,829, which was filed on Apr. 15, 2013.

BACKGROUND OF THE INVENTION

The present invention relates to personal hygiene items, and more specifically, to an improved article such as a tampon having at least one saturation indicator.

Conventional tampons generally include an absorbent material with a permanently attached withdrawal string. A tampon is inserted with or without the aid of an applicator into a woman, with the distal end of the withdrawal string extending outside her vagina. While in use, the tampon prevents leakage of menses. After a period of use, the woman removes the tampon by pulling "downward" on the withdrawal string and replaces the used tampon with a new one, if needed. The "downward" direction is defined herein as the direction opposite to the insertion direction, irrespective of whether the woman is standing, sitting, or prone, i.e. it is the direction that results in extraction of the tampon. Withdrawal strings are intended to be substantially permanently attached to the absorbent material, typically by sewing, hot welding, bonding, and/or adhesively gluing, although they are known to occasionally fail and undesirably detach from the absorbent material.

The FDA regulates tampons, with very strict requirements for the calibration of their absorbency. It moreover requires that women be advised to use the smallest absorbency necessary and to limit the time that a tampon is worn. Improper use of tampons can be a health hazard for a variety of reasons: A too-high absorbency tampon may be kept in place without leakage for an extended length of time, which can lead to toxic shock syndrome. Also, a too-high absorbency tampon may be removed while dry, causing abrasions that increase the likelihood of toxic shock syndrome, since skin wounds are a risk factor. Also, a too-high absorbency tampon is more easily lodged in the vagina. In addition to causing abrasions while attempts are made to remove it, a lodged or stuck tampon is more likely to result in withdrawal cord failure due to the absence of lubricating vaginal fluids that enable removal. In these circumstances, a tampon is more likely to stay in the vagina for an extended length of time before removal, which can lead to toxic shock syndrome.

The proper time for removing a tampon varies by factors such as rate of flow, and absorbency of the tampon. However, since saturation is determined by removal and visual inspection, and reinsertion of a removed tampon is not reasonably accomplished, women can merely guess whether their tampon is nearly dry or alternatively near saturation and in need of removal. As a practical matter they must often decide between removing an unsaturated tampon, or else waiting too long and then suffering the embarrassment and mess associated with leaking menses.

As can be seen, there is a need for an absorbent hygiene article having a saturation indicator. It is desirable that this saturation indicator allows checking the saturation level of an article without removing the article from the wearer. It is desirable that the saturation indicator is calibrated, thereby allowing the user to know when it is too dry to be readily removed, is reaching saturation, or some increment there between. It is desirable that the saturation indicator does not interfere with using the article in the regular manner. It is desirable that this saturation indicator is easy to use, yields an unambiguous reading in a variety of lighting conditions, is easily incorporated into the manufacturing of pre-existing articles, and is economical.

SUMMARY OF THE INVENTION

An improved absorbent hygiene article has a detachably connected saturation indicator. The saturation indicator is preferably calibrated and indicates saturation of the corresponding article by clear demarcation such as staining or swelling. This may be heightened using a coating or surface finish, herein collectively referred to as a "coating". One may check saturation of the hygiene article through visual or tactile inspection of the indicator after it has been pulled out of the article. This may be achieved by pulling a saturation indicator out of the article, and visually observing the indicator, while leaving the remainder of the tampon in place. In this manner it is possible, without having to remove the entire article, to determine whether or not it is advisable to change the article. In one embodiment, the saturation indicator is detachably connected to the underlying article by an adhesive that releases when it becomes moist. In this manner the inability to easily remove the indicator is, in itself, an indication of lack of saturation.

The invention is particularly well suited for incorporation with tampons. In this embodiment at least one saturation indicator is positioned within or on the outside surface of the tampon's absorbent material, approximately parallel to the longitudinal axis of the absorbent body. As the absorbent material becomes saturated with menses, the adjoining saturation indicators become stained, swollen or otherwise exhibit unambiguous features. In order to check saturation of the tampon a wearer locates the free end of the saturation indicator, pulls downwardly, and then performs a visual or tactile inspection of the detached indicator.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

As used herein, the follow structure numbers are associated with the stated structures among the various figures:

10—Tampon;
12—Absorbent material;
14—Withdrawal string;
16—Menses;

20—Saturation indicator;
22—Unmarked portion;
24—Marked portion;
27—Attachment site;
30—Hygiene article;
40—Absorbent material proximal end;
41—Absorbent material distal end;
50—Saturation indicator proximal end; and
51—Saturation indicator distal end.

Broadly, an embodiment of the invention provides an absorbent hygiene article, such as a tampon or diaper, which includes a calibrated, detachably connected saturation indicator. The saturation indicator can be removed to determine how saturated the article is, and whether or not it is necessary to replace the article.

Figure 1:
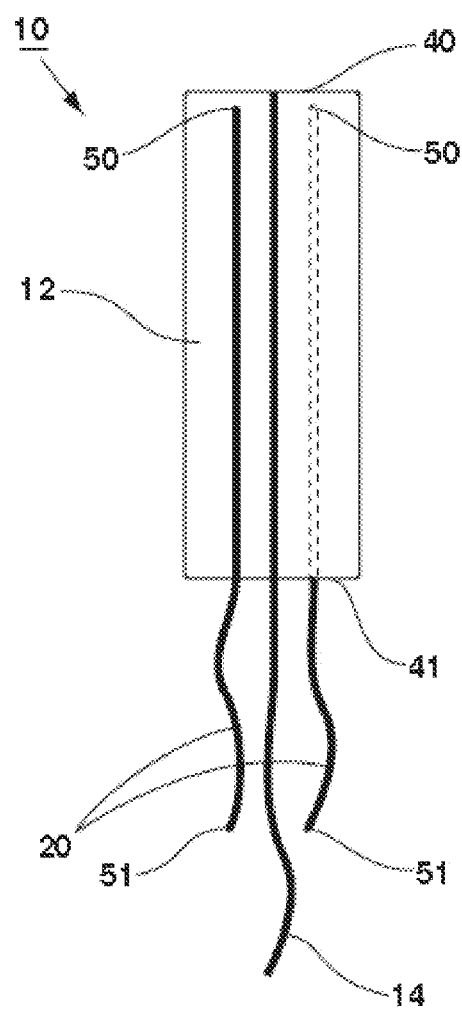
FIG. 1 depicts a tampon embodiment according to the present invention.

Referring to FIG. 1, tampon 10 generally includes absorbent material 12 and withdrawal string 14. Absorbent material is conventionally constructed of a substrate such as rayon, cotton, polyester, spun fibers and combinations thereof, with withdrawal string 14 substantially permanently attached thereto, generally by stitching. Withdrawal string 14 protrudes from absorbent material distal end 41, thereby allowing a user to grasp withdrawal string 14, exert downward force and remove tampon from her vagina.

Tampon 10 of an embodiment of the present invention includes biocompatible and non-toxic saturation indicator 20 which is substantially parallel to longitudinal axis of absorbent material 12. Saturation indicator 20 may be cylindrical, or flattened, and constructed of a variety of flexible and strong materials such as rayon, cotton, polyester, wood cellulose, synthetic polymers and combinations thereof.

Tampons are manufactured from highly absorbent materials that wick moisture. Accordingly, in order to have an effective saturation indicator, the components must be properly calibrated. As used herein, "calibrated" shall mean that the user can readily identify the level of saturation based on distinguishable features on the saturation indicator. These features can be effectuated by a variety of systems including staining; mercerization process; enhanced porosity at regular intervals to achieve stripes or the like; porous regions through the indicator that expand in a manner that allows visual and/or tactile examination of the detached saturation indicator; liquid absorbing excipients such as polyvinylpolypyrrolidone; chemical indicators and biological indicators.

Six thread types manufactured by Coats & Clark (Coats & Clark, Inc. Charlotte, N.C. 28277, USA) were used to demonstrate example calibrations as saturation indicators in two types of commercially available tampons: TAMPAX Pearl and U by KOTEX. The six thread types are: (1) Coats & Clark DUAL DUTY PLUS for Buttons and Crafts (color 1, white): 74% polyester, 26% cotton glacé finish. (The Coats & Clark's proprietary polished glacé finishing process reduces thread tangling and abrasion.) Tex size 104; (2) Coats & Clark mercerized Egyptian Giza Extra Long Staple (ELS) cotton for Machine Quilting & Crafts (color 1, white): 100% cotton. Tex size 35; (3) Coats & Clark SURELOCK for overlock machines (color 0400, white): 100% spun polyester. Tex size undetermined, but appears to be approximately 20-30; (4) Coats & Clark DUAL DUTY PLUS, for Hand Quilting, Thread color (001, white), 68%, 32% glacé cotton finish. Tex size 40; (5) Coats & Clark 100% cotton for Hand Quilting, Thread color (100, white), 100% glacé cotton finish. Tex size 50; and (6) Coats & Clark, "Cotton Covered", for Quilting and Piecing, Thread Color (150, off-white), 65% polyester, 35% cotton. Tex size 30.

In a calibration procedure, the six different types of thread were used in two different types of Regular size tampons, for seven different saturation levels that ranged from 0 to approximately 10 g of absorbed liquids. As used herein, "Regular" size tampons are regulated to have absorbency falling in the range 6-9 g per FDA guidelines. Each of the brands was observed to readily absorb 9 g of fluid with no excess leakage A SINGER hand sewing needle was used to pull thread through the tampons for each of the six types of thread. The threads were inserted lengthwise into the absorbent material distal end 41 of each tampon and then pulled out through the absorbent material proximal end 40, leaving 5-10 cm lengths of thread extending out of both ends of the absorbent material. The threads extending out of proximal end 40 were then cut off flush with the proximal end of the absorbent material 40. The threads extending out of the distal end 41 of the absorbent material were cut off at a length comparable to that of the withdrawal string. One teaspoon of BETTY CROCKER red gel dye was dissolved in 6 oz of tap water and then measured portions of the dyed water were transferred into 6 shot glasses in the amounts of ¼, ½, ¾, 1, 1½ and 2 teaspoons. Tampons were then placed in the shot glasses until the dyed liquid was totally absorbed. The threads were removed 15 minutes later, and the stain height was recorded. It should be noted that the staining pattern was very characteristic of the thread-tampon combination employed, in terms of the stain intensity, its length and the uniformity of the stain pattern. Only the height of the stain pattern is listed in the tables.

Figure 5:
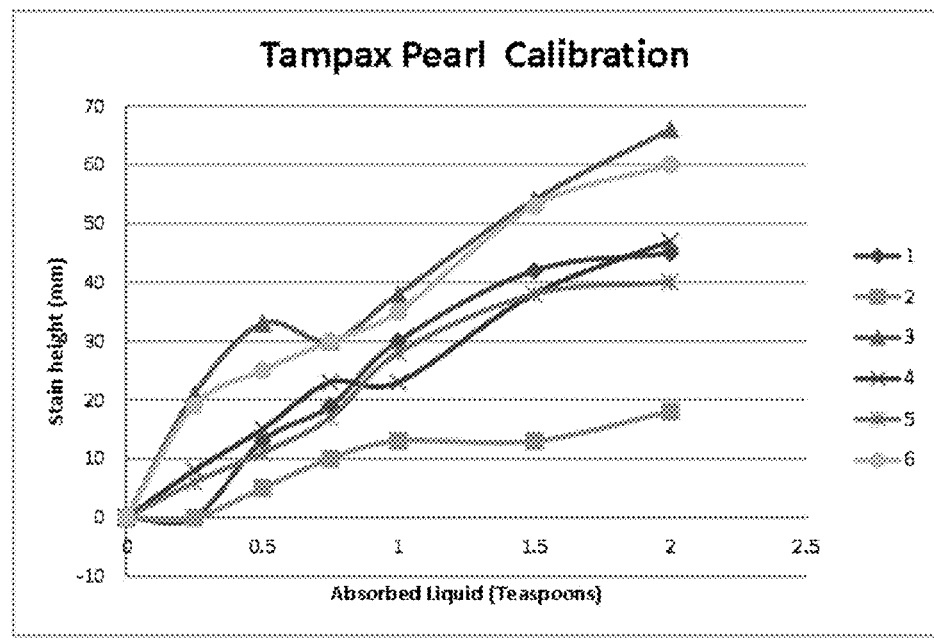
FIG. 5 graphically reports the calibration of various string types in a commercially available tampon.
Figure 6:
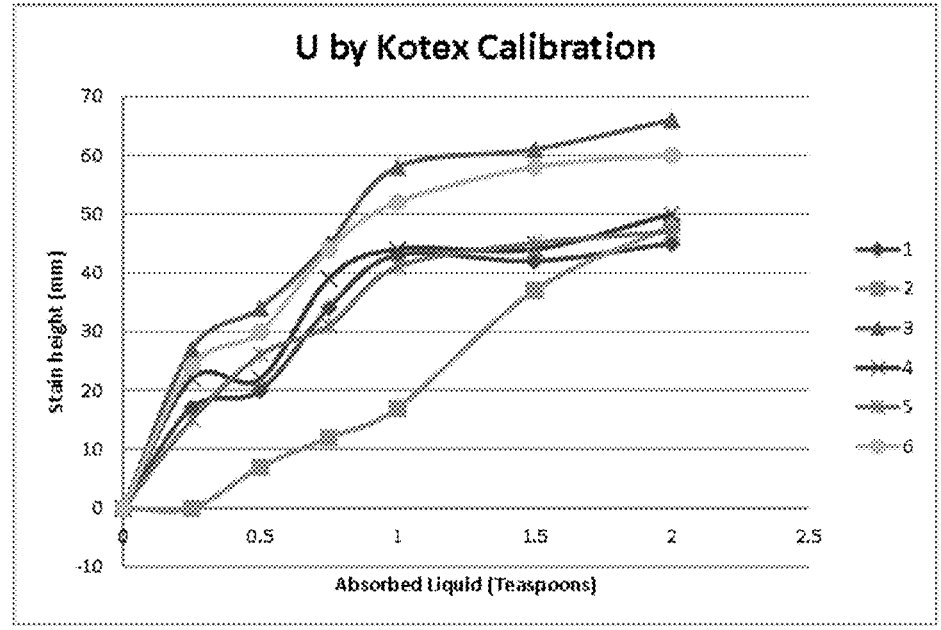
FIG. 6 graphically reports the calibration of various string types in a different commercially available tampon.

Most notable in the calibration results is that threads with similar finishes and wicking properties exhibit similar calibration curves: For example, the cotton glacé finish threads (1), (4) and (5) were observed to exhibit little to no wicking when immersed directly in dyed water and their calibration curves fall close to each other for each of the two tampons studied. Threads that exhibited high degrees of wicking when immersed directly in the dyed water (3) and (6) also fell close to each other in the calibrations for each of the two tampons studied. The data is reported as Table 1 and Table 2, and graphically represented in FIGS. 5 and 6:

TABLE 1

| Tampax Pearl Regular Absorbed Liquid | Height of stain pattern in millimeters for 6 thread types | | | | | |
|---|---|---|---|---|---|---|
| (teaspoons) | 1 | 2 | 3 | 4 | 5 | 6 |
| 0 | 0 | 0 | 0 | 0 | 0 | 0 |
| 0.25 | 0 | 0 | 21 | 8 | 6 | 19 |
| 0.5 | 13 | 5 | 33 | 15 | 11 | 25 |
| 0.75 | 19 | 10 | 30 | 23 | 17 | 30 |
| 1 | 30 | 13 | 38 | 23 | 28 | 35 |
| 1.5 | 42 | 13 | 54 | 38 | 38 | 53 |
| 2 | 45 | 18 | 66 | 47 | 40 | 60 |

TABLE 2

| U by Kotex Regular Absorbed Liquid | Height of stain pattern in millimeters for 6 thread types | | | | | |
|---|---|---|---|---|---|---|
| (teaspoons) | 1 | 2 | 3 | 4 | 5 | 6 |
| 0 | 0 | 0 | 0 | 0 | 0 | 0 |
| 0.25 | 17 | 0 | 27 | 22 | 15 | 24 |
| 0.5 | 20 | 7 | 34 | 22 | 26 | 30 |
| 0.75 | 34 | 12 | 45 | 39 | 31 | 44 |
| 1 | 43 | 17 | 58 | 44 | 41 | 52 |
| 1.5 | 42 | 37 | 61 | 44 | 45 | 58 |
| 2 | 45 | 48 | 66 | 50 | 47 | 60 |

As shown in FIG. 1, saturation indicator 20 can be positioned within, or located on the outside surface, of absorbent material 12, with saturation indicator distal end 51 protruding out of absorbent material distal end 41. It is desirable that saturation indicator distal end 51 protrudes approximately 5 to 10 cm beyond absorbent material distal end 41. Saturation indicator proximal end 50 may be in close proximity (within 1 cm) to absorbent material proximal end 40, so saturation indicator yields a reading that reflects the actual saturation.

Figure 2:
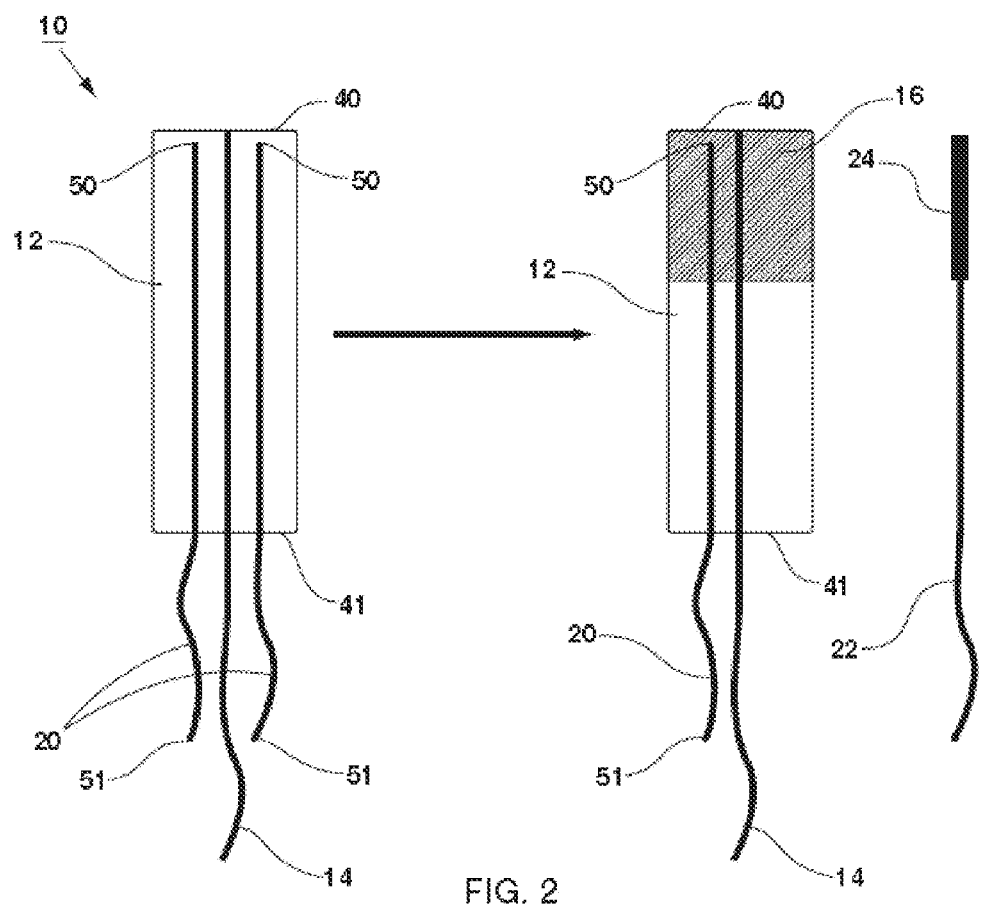
FIG. 2 depicts an unsaturated tampon with intact saturation indicators, then a partially saturated tampon with one stained saturation indicator removed.

Referring to FIG. 2, unsaturated tampon 10 is depicted on the left. As shown on the right, upon the absorbance of menses 16, removed indicator would depict marked portion 24 which corresponds with saturation, and unmarked portion 22 which corresponds with lack of saturation. In this manner a user can quickly and easily ascertain the extent of saturation of her tampon, and determine whether or not tampon removal is appropriate.

Determining the appropriateness of removal could be based on a predetermined threshold, or independent decision making. By way of example, 90% saturation could be established as the saturation threshold, and the saturation indicator could be likewise pre-marked (not shown).

It is important that saturation indicator 20 is detachably connected to absorbent material 12. As used herein, "detachably connected" shall mean that the indicator remains attached to the absorbent material while a woman is wearing the improved tampon, but that the indicator can be removed by the woman grasping the indicator, and exerting reasonable downward force on it. Such force may slightly tug at the absorbent material prior to breaking free, but not displace the absorbent material within the vagina.

Figure 3:
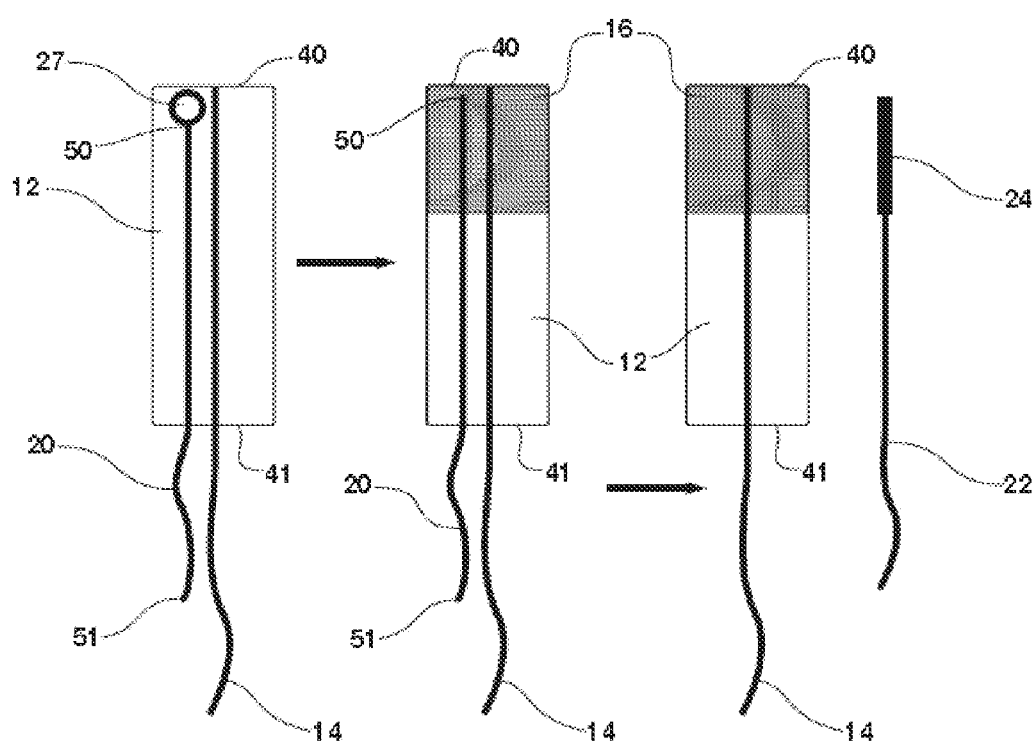
FIG. 3 depicts an unsaturated tampon with an adhered saturation indicator, then the dissolution of the adhesive when moistened by menses, then saturation indicator removed.

In one embodiment, shown in FIG. 3, attachment site 27 is an adhesive that releases when it becomes moist. In this manner the saturation indicator would be firmly attached to unsaturated absorbent material, such that a user's inability to detach the saturation indicator using reasonable force would, in and of itself, indicate lack of saturation beyond a predetermined threshold. Subsequent saturation of the absorbent material, shown stepwise in FIG. 3, would release or dissolve the adhesive of attachment site 27, thereby allowing removal of saturation indicator with reasonable force. The saturation indicator could be glued into the absorbent material with the adhesive at the attachment site 27, or alternatively a portion of the proximal end of the saturation indicator 50 could be finished or coated with materials that adhere when dry and allow the indicator to slip out when moist. Examples of suitable adhesives for the attachment site 27 include Lineco Methyl Cellulose Adhesive, a neutral pH, non-toxic water reversible adhesive (Lineco, Inc., Holyoke, Mass. 01041, USA); METHOCEL Cellulose Ethers, (Dow Chemical Company, Midland, Mich. 48674, USA) which are methylcellulose and hydroxypropyl methylcellulose rheology modifiers; and/or ETHOCEL (Dow Chemical Company, Midland, Mich. 48674, USA) which are ethylcellulose organosoluble polymers for binding, coatings and rheology modification. Examples of suitable coating materials for the saturation indicator, and in particular proximal end of saturation indicator, include polyvinyl-pyrrolidone coated with sodium chloride (which forms a thick and slippery layer when it becomes moistened) and/or pointed surface structures on the indicator that grip only when dry and materials used for absorbable sutures, such as polyglycolic acid, a biodegradable polymer. Saturation indicator 20 may indicate saturation by a variety of mechanisms including staining, discoloration, swelling, and chemical reactions. Resulting indications may be solid, patterned, or textured. An enhancing coating (not shown) may be used in conjunction with saturation indicator 20 to yield a more robust demarcation than staining alone. In order to avoid confusion between withdrawal string 14 and saturation indicator 20 it is desirable that the structures are readily distinguishable by having different properties such as diameters, colors, textures, lengths and combinations thereof.

Figure 4:
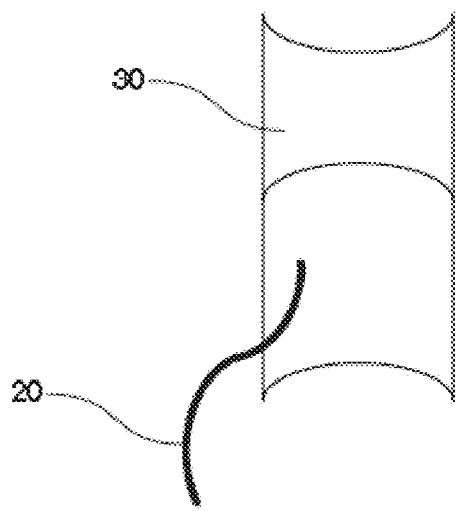
FIG. 4 depicts a diaper having a saturation indicator.

While the present invention has been discussed in depth in conjunction with a tampon, it should be understood that the technology could be applied to a variety of absorbent hygiene articles for both humans and animals, including diapers, adult incontinence shields, medical diagnostics of the fluids and biological or chemical species that the indicators are exposed to, including pregnancy indicators, and for use with absorbent mats and pad materials for spills and drainage control in residential, industrial and commercial settings. FIG. 4 depicts one such alternative embodiment, with saturation indicator 20 incorporated with absorbent hygiene article 30 being a diaper.

The saturation indicator may be constructed in a variety of designs and colors, and include anti-odor, anti-fungal, anti-microbial properties, anti-wick and/or moisture release characteristics. These properties may be imparted by a coating or finish. The saturation indicator may be branched or helical within the interior of the tampon so as to simultaneously sample cross-sections of the absorbent material, and it may include features such as local capillary trapping of liquid to enhance staining and/or swelling in a regular pattern, standard mercerization processes, etc. It may exit the tampon through the interior of the withdrawal cord, as the cord is typically formed from a loose configuration of intertwined strands. It may also be fabricated from threading materials used for surgical sutures. The indicator may be formed from a composite of materials, for example so that a transition to a non-wicking material may be used for portions exterior to the tampon.

It should be understood, of course, that the foregoing relates to exemplary embodiments of the invention and that modifications may be made without departing from the spirit and scope of the invention as set forth in the following claims. By way of example, the FIGS. depict single and dual indicators, but it is possible to include any number of indicators in a tampon. It should also be understood that ranges of values set forth inherently include those values, as well as all increments between. Finally, unless otherwise noted, or if contrary to common sense, all approximations shall be +/−5%.

What is claimed is:

1. An improved tampon including:
   a. An absorbent material having a proximal end and a distal end;
   b. A withdrawal string substantially permanently attached to said absorbent material; and
   c. A saturation indicator detachably connected to said absorbent material and extending beyond said distal end, said saturation indicator proportionally indicative of menses saturation in said absorbent body.

2. The improved tampon of claim 1 wherein said saturation indicator is substantially parallel to the longitudinal axis of said absorbent material.

3. The improved tampon of claim 2 where said saturation indicator is readily distinguishable from said withdrawal string.

4. The improved tampon of claim 3 wherein said saturation indicator and said withdrawal string are distinguishable by at least one property selected from diameter, color, texture, length and combinations thereof.

5. The improved tampon of claim 1 wherein said saturation indicator is detachably connected to said proximal end by adhesive.

6. The improved tampon of claim 5 wherein said adhesive releases when it becomes moist.

7. A method of reducing the frequency of tampon replacement including the steps of:

Inserting a tampon having an absorbent material with a proximal end and a distal end; a withdrawal string substantially substantially permanently attached to said absorbent material; and an elongated saturation indicator detachably connected to said absorbent material and extending beyond said distal end, said saturation indicator proportionally indicative of menses saturation in said absorbent body;

Allowing said tampon to absorb menses; and

Exerting downward force on said saturation indicator.

8. The method of claim 7 wherein said step of exerting downward force further includes the step of detaching said saturation indicator from said absorbent material.

9. The method of claim 8 further including the step of determining if said saturation indicator has reached a threshold saturation level.

10. The method of claim 9 further including the step of removing the remainder of said tampon in response to a determination that said threshold saturation level has been reached.

11. The method of claim 7 further including the step of keeping the remainder of said tampon in place in response to a determination that said threshold saturation level has not been reached.

12. The method of claim 8 wherein said step of exerting downward force further includes the steps of detecting resistance and ceasing the exertion of downward force.

13. A method of reducing incidents of tampon oversaturation and leakage including the steps of:

Inserting a tampon having an an absorbent material with a proximal end and a distal end; a withdrawal string substantially substantially permanently attached to said absorbent material; and elongated saturation indicator detachably connected to said absorbent material and extending beyond said distal end, said saturation indicator proportionally indicative of menses saturation in said absorbent body;

Allowing said tampon to absorb menses; and

Exerting downward force on said saturation indicator.

14. The method of claim 12 wherein said step of exerting downward force further includes the step of detaching said saturation indicator from said absorbent material.

15. The method of claim 12 further including the steps of determining if said saturation indicator has reached or exceeded a threshold level of saturation.

16. The method of claim 15 further including the step of removing the remainder of said tampon in response to a determination that said threshold saturation level has been reached or exceeded.

* * * * *